United States Patent [19]
Ramos Martinez

[11] Patent Number: 5,178,634
[45] Date of Patent: Jan. 12, 1993

[54] AORTIC VALVED TUBES FOR HUMAN IMPLANTS

[76] Inventor: Wilson Ramos Martinez, Doctor Fleming, 24, Madrid, Spain

[21] Appl. No.: 765,000

[22] Filed: Sep. 24, 1991

Related U.S. Application Data

[63] Continuation of Ser. No. 461,056, Jan. 4, 1990, abandoned.

[30] Foreign Application Priority Data

Mar. 31, 1989 [ES] Spain .................................. 8901122

[51] Int. Cl.⁵ .......................... A61F 2/24; A61F 2/04
[52] U.S. Cl. ............................................ 623/2; 623/1; 623/12
[58] Field of Search ........................ 623/1, 2, 12, 11, 66

[56] References Cited

U.S. PATENT DOCUMENTS

| | | | |
|---|---|---|---|
| 3,626,947 | 12/1971 | Sparks | 623/1 X |
| 3,966,401 | 6/1976 | Hancock et al. | 623/2 X |
| 4,728,328 | 3/1988 | Hughes et al. | 623/1 |
| 4,787,901 | 11/1988 | Baykut | 623/2 |
| 4,842,575 | 6/1989 | Hoffman, Jr. et al. | 600/36 |
| 5,084,065 | 1/1992 | Weldon et al. | 623/1 |

OTHER PUBLICATIONS

Complete Replacement of the Ascending Aorta with Reimplantation of the Coronary Arteries by C. Cabrol et al. The Journal of Thoracic and Cardiovascular Surgery, vol. 81, No. 2, Feb. 1981, pp. 309–314.
Cardiac Surgery by John W. Kirklin et al., Chapter 54, ACUTE AORTIC DISSECTION pp. 1471-1491.
Primary Repair of Acute Ascending Aortic Dissection by Gordon N. Olinger et al. The Annals of Thoracic Surgery, vol. 44, No. 4, Oct. 1987, pp. 389-393.
Repair of Ascending Aortic Disscretion by R. Kent Jex et al. The Journal of Thoracic and Cardiovascular Surgery, vol. 93, No. 3, Mar. 1987, pp. 375-382.
Extended Aortic Root Replacement with Aortic Allografts by Robert L. McKowen et al. The Jounral of Thoracic and Cardiovascular Surgery, vol. 93, No. 3, Mar. 1987, pp. 366-373.

Primary Examiner—Randall L. Green
Assistant Examiner—D. Willse
Attorney, Agent, or Firm—Darby & Darby

[57] ABSTRACT

An aortic valved tube which is used in human implants to replace the corresponding cardiac valve and ascending section of the aorta itself, incorporates a cardiac valvular prosthesis in its proximal end. The valved tube has two integral branches which project from opposite points with an inclination relative to the longitudinal axis of the tube, which branches are for effecting the anastomosis of the ostiums, corresponding to the left and right coronary arteries, respectively. The branches, as well as the sectors above and below the branches, are reinforced by a thicker wall in those areas while, maintaining the inside diameter of the tube itself.

6 Claims, 3 Drawing Sheets

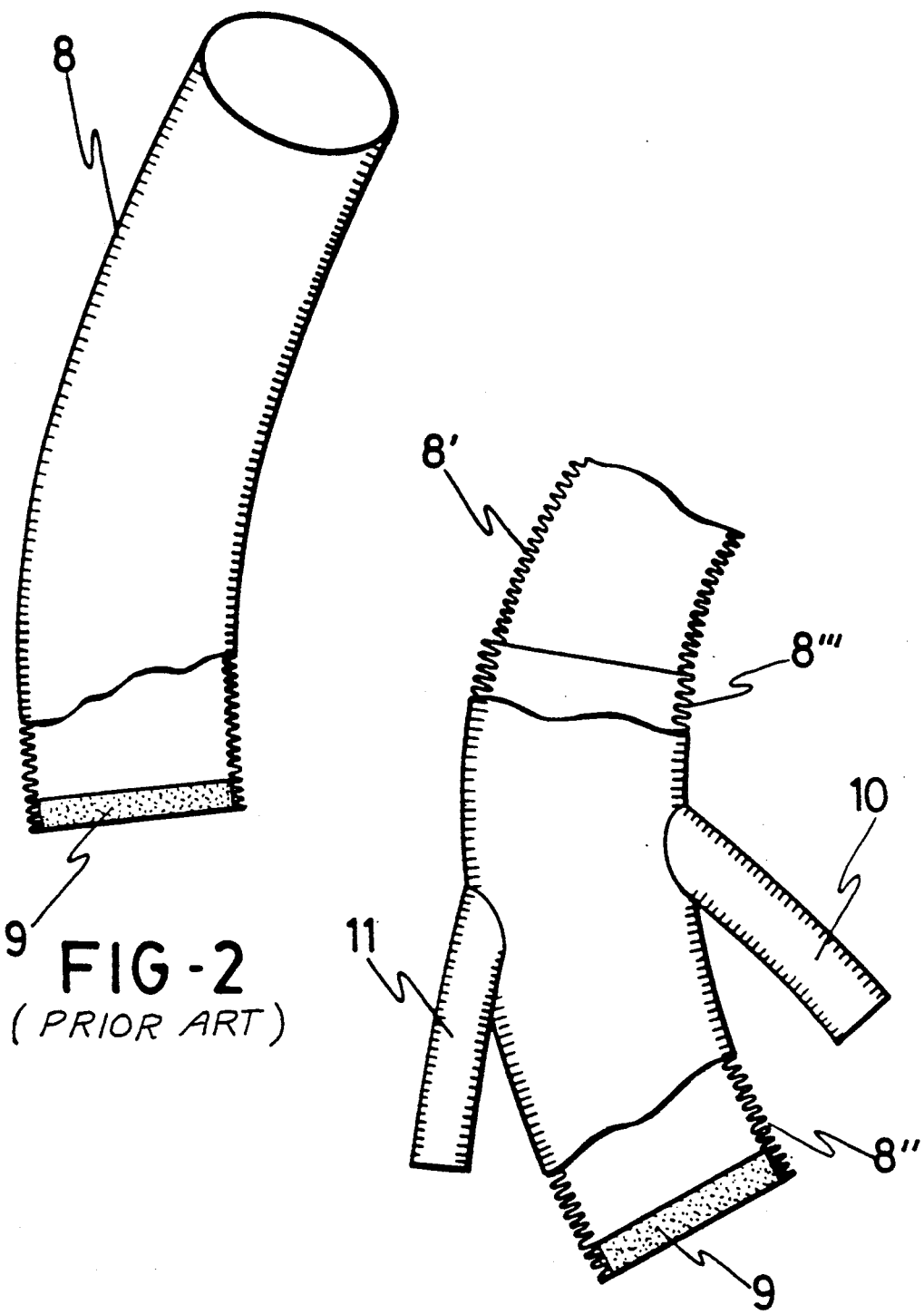

AORTIC VALVED TUBES FOR HUMAN IMPLANTS

This is a continuation of application Ser. No. 461,056, filed Jan. 4, 1990, now abandoned.

OBJECT OF THE INVENTION

The present invention refers to aortic valved tubes that are used as an element of replacement of the aorta for human implants, to tubes which are manufactured out of a material known as DACRON, polyester synthetic fiber impregnated in low porosity collagen, each tube also including a metal cardiac valvular prosthesis, which is implanted inside and in correspondence with the proximal end of the tube itself.

The object of the invention is centered on some improvements introduced in this type of aortic valved tubes, one of the improvements consisting of the incorporation of two branches as integral extensions from the tube itself, the branches being intended for connection to the right and left coronary arteries. An advantage consists of the structure of the tube itself incorporating a reinforcement in correspondence with the infracoronary and supracoronary sector.

BACKGROUND OF THE INVENTION

In certain clinical settings it is necessary to implant an aortic valved tube which, incorporating a cardiac valvular prosthesis, is used to replace the aortic valve and the aorta itself in its ascending path.

These clinical settings are known by the following names:
"Acute dissection of the ascending aorta"
"Marfan's syndrome"
"Traumatic breakage of the ascending aorta affecting the aortic valve and the right and left coronary arteries."

Surgical treatment of these clinical settings dates back some fifty years, during which techniques and methods, as well as the implant models, have improved, though a suitable physiological model has not been attained up to now.

In this sense, the first attempts were made by implanting a tube made out of special fiber, replacing the torn or broken aorta sector, without replacement of the aortic valve.

Subsequently, implant models with the valvular prosthesis incorporated in the tube came about, and this is the present situation.

On the other hand, the anatomico-pathological setting of acute dissection of the ascending aorta can be summarized in the following: upon producing breakage of the intima layer of the aorta, blood penetrates in the thickness of the layers of said artery, making a dissection among them, causing hemorrhage and compression.

Almost always associated with this problem is an aortic bicuspid valve of congenital origin, needing replacement.

The clinical setting is completed with the dislocation of the coronary arteries and, at times, with dissection thereof.

This clinical setting is necessarily dramatic and fatal if surgical repair is not rapidly and urgently done.

Said surgery is based on "reconstruction" of the aortic valvular ring of the involved ascending aorta sector and "reimplantation" of the coronary arteries: right and left.

The implant element in the surgery is the above cited aortic valved tube, which comprises a single tube with a cardiac valvular prosthesis implanted inside it, and in correspondence with the proximal end thereof.

When using this aortic valved tube, upon having to "reimplant" the left and right coronary arteries, two holes must be made in the wall of the valved tube, and these holes must be "adapted" to the holes of the ostiums of the corresponding coronary arteries.

Such operations involve the difficulties that the holes made in the wall of the valved tube may not be uniform with their surroundings, aside from having a weak structure.

On the other hand, anastomosis causes distortion of the tube, leaving a residual "asymmetric" traction.

As a result of this post-anastomosis, hemorrhage is frequent and, many times, it is the main cause of post-operative death in this type of surgery.

It is also to be taken into account that when the dissection has been very great and the coronary arteries have been greatly dissected, it is practically impossible to carry out anastomosis from a technical point of view. Such procedure produces distortion of the valved tube, with the subsequent defect of the suture, with undue tractions, with alterations in the bloodstream, as well as distortions in the functioning of the prosthesis incorporated in the valved tube.

Finally, it should be said that by means of said known aortic valved tube, the patient's aortic valvular problem is corrected, as well as the ascending aorta section implicated in the breakage. Now then, there is no doubt that the ostiums of the coronary arteries must still be "brought near" the valved tube, where said two holes have to be made in order to be able to bring it close to the edges of the coronary ostiums. Upon effecting said operation, breakage of the integrity of the tube, of its structure, is produced, likewise producing on many occasions small dilacerations which later produce tearing and cause hemorrhaging.

On the other hand, because it is practically impossible that the holes be made symmetrically, asymmetric tractions will be produced which distort the location of the tube, with the subsequent detriment to its functioning.

In the case of hemorrhage, once the tube has been implanted and the coronary arteries have been coupled, it becomes very complicated and difficult to act with surgical delicateness when necessary to give some additional stitches and, generally, the entire suture is dislocated causing hemorrhage and obstruction in the lumen of the coronary ostiums.

Due to all of this, the duration of the surgery is considerably lengthened due to the sutures being hard to make and with little space to use the instruments without distorting the structure of the tube itself.

DESCRIPTION OF THE INVENTION

In order to solve all these problems and inconveniences, the invention proposes a series of improvements of the cited aortic valved tube, which definitively solve said types of alterations in the system of implants which we are referring to.

These improvements give rise to an aorto-coronary valved tube which has a different structural make-up, physiological base and integral concept of the anatomic similarity of the vasculo-valvular structures of the anatomic area in question, specifically the aortic valved root and initial section of the ascending aorta.

Said tube, according to the object of the invention, has, in continuity with the original tube itself, two branches, as integral derivations, directed to the coronary arteries: right and left.

On the other hand, the tube in question also has the novelty that it includes a reinforcement of the infracoronary and supracoronary sector, or what is the same, a reinforcement of the supra-valvular and valvular sector.

This reinforcement is obtained, not based on and at the expense of the architectural structure itself of the tube, but with an increase of the thickness of the wall in said areas.

On the basis of this new concept of the aorto-coronary valved tube, anastomosis of the coronary ostiums is effected without any type of difficulty, also obtaining a good operation.

In the same way, the areas corresponding to the valvular sector and the supra-valvular sector, as well as the supra-coronary sector, are reinforced. This gives rise to the tube being more static to the bloodstream, avoiding with this the dislocation or distortion of the arrangement of the two branches directed to the coronary arteries, above all, the one branch directed to the branch of the left coronary artery, due to its posterior position and remaining between the tube and the posterior wall itself of the patient. This reinforcement permits no degree of pseudo-collapse by pressure and impulsion of the tube on the posterior wall of the aorta itself of the patient.

On the basis of the drawings that are seen on the sheet of figures which are attached, and with the help of the description which is made hereinafter, the features or improvement objectives of the invention will be more easily understood.

BRIEF DESCRIPTION OF THE DRAWINGS

FIG. 2 shows another schematic general view of a conventional aortic valved tube, which is presently used in the implants referred to throughout the entire present description.

FIG. 3 shows a schematic view of the partially cut away aortic-coronary valved tube made in accordance with the invention, wherein one can clearly see the two branches for the ostiums of the right and left coronary valves, as well as the reinforcement that the tube has in the areas corresponding to the infracoronary and supracoronary sectors.

DESCRIPTION OF THE PREFERRED EMBODIMENT

Figure 1:
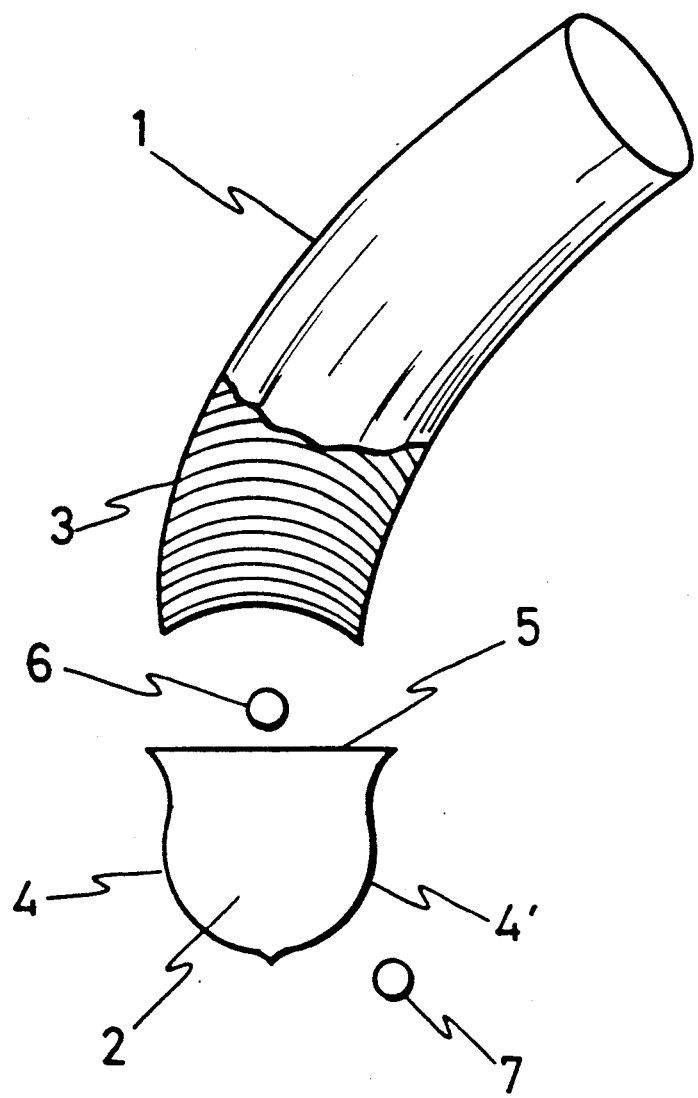
FIG. 1 shows a schematic general view corresponding to the real anatomic location of the aortic root, its corresponding valve and the ostiums corresponding to the right and left coronary arteries.

In the first place, mentioning FIG. 1, one can see in the real anatomic position of an aortic root, in which the ascending aortic section 1 is distinguished, the corresponding valve 2 and between both an aortic section which specifically corresponds to the posterior wall 3. As can be seen in this FIG. 1, the aortic valve 2 includes valvae 4, 4' and 5 which correspond to the "non coronary," "right coronary" and "left coronary", respectively.

In this same way, the ostiums 6 and 7 corresponding to the left and right coronaries, respectively, are observed.

Presently, when an implant is effected the aortic valved tube 8, shown in FIG. 2, is intercalated. This is conventional. In its proximal end it includes the preferably metallic aortic valvular prosthesis 9 in such a way that with that tube 8 and this prosthesis 9, the aortic valvular problem and the ascending aortic section involved in a failure are corrected.

Now then, in the corresponding operation it is necessary to "bring" the ostiums 6 and 7 represented in FIG. 1 "near" said valved tube 8, for which it is necessary to make in the latter two holes in order to be able to adapt it to the coronary ostiums. Upon effecting said operation, breakage of the integrity of the structure of the tube 8 is produced. On numerous occasions small dilacerations which later produce tears and cause hemorrhages are produced.

On the other hand, it is practically impossible to make symmetric holes in that tube 8. Therefore, asymmetric traction which distorts the position of the tube itself, with the subsequent detriment to its operation, is produced.

In the event that hemorrhaging is caused, once the tube 8 has been implanted and the ostium have been brought near, it is very complicated and difficult to be able to act with surgical delicateness upon having to give some additional stitches and, generally, the entire suture is dislocated causing hemorrhage and obstruction in the lumen of the coronary ostiums.

All of this greatly lengthens the duration of the operation since it is difficult to make sutures and there is little space to use the instruments without distorting the structure of the tube itself.

Now then, as a result of all of these problems and inconveniences which are brought about by implantation based on the tube 8 with the valvular prosthesis 9, a new tube with some improvements by which all of these problems and inconveniences are eliminated, has been conceived.

Figure 4:
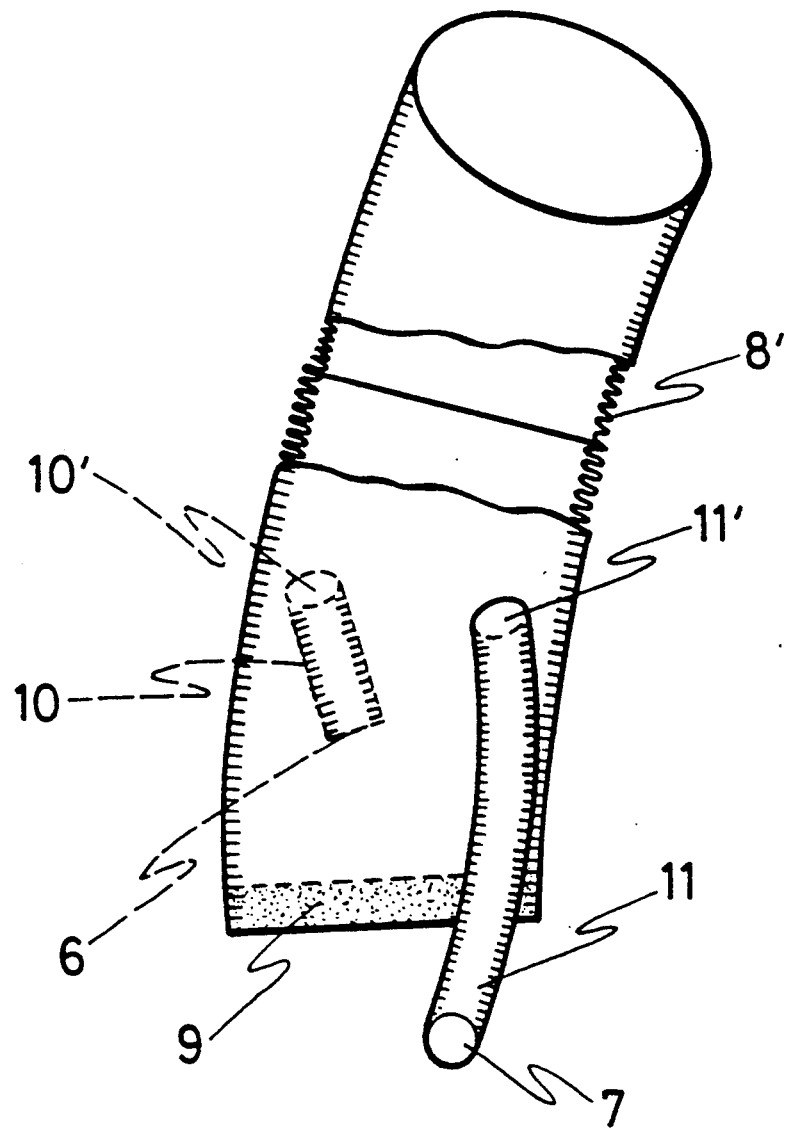
FIG. 4 shows the aorta-coronary valved tube represented in the previous figure, used as an implant, in other words, with its integral branches over the ostium of the right and left coronary valves.

Tube 8', just as it is made in accordance with the object of the invention, is shown in FIGS. 3 and 4. It is made out of the same material as the conventional tube 8 but it has two basic novel features:

1. Said tube 8' has two branches 10 and 11 as an integral continuity of the tube itself 8', branches 10 and 11 for the "approximating" of the ostium 6 and 7.

Tube 8' made in accordance with the object of the invention, includes the corresponding valvular prosthesis 9 just as the conventional tube 8 included it.

Another novel feature or improvement of the tube 8' is that certain areas are reinforced and these areas correspond precisely to the branches themselves 10 and 11 derived from the tube 8', to sector 8" included between the branches and the proximal end, and to a sector 8'" provided after branches 10 and 11. This reinforcement protects the supravalvular and valvular sectors of implantation of the cardiac valvular prosthesis, or what is the same, the infracoronary and suprcoronary sectors.

The reinforcement of sectors 8" and 8'" and of the derived branches themselves 10 and 11, is attained not at the expense of the structure itself of the original tube 8', but simply by increasing the thickness of the wall in those areas or sectors. The inside caliber remains without any variation, in other words, the thickness of the wall only increases with regard to the outside surface since the inside diameter of the tube and of its branches remain constant.

As an example and as an ideal one, the inside diameter of the aorto-coronary valved tube which is being described will be approximately 30 mm. and its ideal length will be 20 cm., while the ideal diameter of the branches 10 and 11 will be 8 mm.

On the basis of these novel features, the following advantages are obtained:

Upon extending, as an integral branch of the original tube, branches 10 and 11 for the ostiums 6 and 7 from the right and left coronary arteries, the holes 10' and 11' in the valved tube 8' remain perfectly "beveled" without tears or abnormal loss of continuity, without wrinkles, without protuberances, without possible traumatic areas which can be the beginning of a hypothetical thrombotic process at that level. Besides there is also an oblique sector which is in accordance with the geometric anatomic shape itself of the right and left coronary arteries where they begin in the aortic wall.

This construction leads to a better blood flow, avoiding the need to make two coupling sutures and consequently eliminating the possibility of post-operative hemorrhage.

Likewise the surgical time is reduced, and in this type of operation this is essential and vital.

Intracoronary circulation is also made more physiological by the described valved tube.

As the tube 8' has a certain flexibility, due to the material it is made of, as has been expressed at the beginning of the present specification, coupling for the coronary arteries will be easier, since the orientation and direction which can be given to each one of the branches 10 and 11 remains at the surgeon's discretion and depends on the circumstances which are observed in the operative field in each particular case.

On the other hand, it is known that positioning of the beginnings of the branches 10 and 11 intended for coupling to the coronary arteries has to be effected, or rather, is preferably made, 2 cm. above the implantation of the cardiac valvular prosthesis 9. It is totally physiological and its irrigation in the normal cardiac cycle is facilitated, even with a different structural situation.

The fact that the two said branches 10 and 11 emerge from the original tube 8', practically at the same height, but with a different situation and implantation site is also noteworthy.

In connection with the cited reinforcements of the tube 8', they are effected on the basis of the following:

It is known that the systolic impulsion of the blood flow coming from the left ventricle of the human heart generates a systolic pressure of about 130 mm. of mercury in each contraction and subsequent ejection, in such a way that this impulsion suffices to open the aortic valvular prosthesis, making the blood flow break into the lumen of the tube and in its wall and be distributed throughout the entire vascular system of the body.

Obviously, then the maximum pressure of this impulsion is produced or has its effects:

1. On the aortic valvular ring itself of the patient and on his own valve, proceeding to open it and giving free passage to the blood flow.
2. On the valvular and infravalvular sector
3. On the supra-valvular sector when the blood flow has already acquired obstacle free fluidity.

It should also be taken into account that the wall of the tube 8' upon being flexible and dynamic enters into the function of "action-reaction" which the blood stream under pressures subjects it to.

Now then, for all these reasons the reinforcement of tube 8', and specifically in said areas has been provided for. Upon having more contention hardness due to its increase of structure, it is possible for the tube to resist, with a better static position, the systolic blood impulse and, therefore, it will not distort the position of the branch directed to any of the two coronary arteries, above all to the one that is destined to the left coronary artery due to its location behind the valved tube.

This will prevent compression and pseudo-collapse of said branch of the tube from taking place in such a way that said reinforcement will help it maintain its consistency and therefore a non-deformable position.

I claim:

1. An artificial aortic valved tube implant manufactured of biocompatible material for a human for replacing the aortic valve and an ascending section of the human aorta, comprising:
   a tube of generally circular cross section having a proximal end and a distal end, said tube by a tube wall defining a single continuous flow passage between said ends;
   a cardiac valvular prosthesis located within said tube at said proximal end, said flow passage having a substantially constant flow area from said prosthesis to said distal end;
   a first tubular branch and a second tubular branch, each said branch intersecting and extending transversely at different locations from said tube wall and being integral therewith, the interiors of said branches communicating with the interior of said tube through respective holes in said wall, said branches being located on said wall to facilitate subsequent connection of said branches respectively to the left and right coronary arteries of said human,
   sections corresponding to the infracoronary and supercoronary sectors of said tube being reinforced, the thickness of the wall outward from said flow passage, being greater at those reinforced sections than that at the distal end of the tube.

2. An aortic valved tube implant for human implants, according to claim 1, wherein both of said branches are approximately at the same distance from the proximal end of said tube, said branches being inclined to said tube wall at the holes, said holes having an oblique section generally corresponding with the anatomic-geometric shape of the coronary arteries of the human at the beginnings of said arteries at the patient's aortic wall.

3. An aortic valved tube implant for human implants, according to claim 1, wherein each of said branches has the thickness of its respective wall reinforced, said thickness reinforcement beginning at said holes.

4. An aortic valved tube implant as in claim 1, wherein said branches are positioned approximately 2 centimeters from said proximal end of said tube.

5. An aortic valved tube implant as in claim 1, wherein said branches have a diameter in the order of 8 millimeters.

6. An aortic valved tube implant as in claim 1, wherein said holes in said tube wall at the intersections with said branches are generally oval in shape, said branches extending from said walls obliquely toward said proximal end of said tube, an acute angle being formed between each said branch and said tube in the direction of said proximal end.

* * * * *